(12) United States Patent
Poplow (10) Patent No.: US 11,203,566 B2
(45) Date of Patent: Dec. 21, 2021

(54) HYDROGENATION OF AROMATIC COMPOUNDS (71) Applicant: BASF SE, Ludwigshafen (DE)

(72) Inventor: Frank Poplow, Ludwigshafen (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 16/624,338

(22) PCT Filed: Jul. 17, 2018

(86) PCT No.: PCT/IB2018/055292
§ 371 (c)(1),
(2) Date: Dec. 19, 2019

(87) PCT Pub. No.: WO2019/008561
PCT Pub. Date: Jan. 10, 2019

(65) Prior Publication Data
US 2021/0032189 A1 Feb. 4, 2021

(30) Foreign Application Priority Data
Jul. 5, 2017 (EP) .................................. 17179827

(51) Int. Cl.
C07C 67/303 (2006.01)
B01J 19/18 (2006.01)
(Continued)

(52) U.S. Cl.
CPC ......... C07C 67/303 (2013.01); B01J 19/1837 (2013.01); B01J 19/1843 (2013.01);
(Continued)

(58) Field of Classification Search
None
See application file for complete search history.

(56) References Cited

U.S. PATENT DOCUMENTS 6,284,917 B1  9/2001  Brunner et al.
7,361,714 B2  4/2008  Grass et al.
(Continued)

FOREIGN PATENT DOCUMENTS

DE   10036172 A1   3/2001
DE   10225565 A1   12/2003
(Continued)

OTHER PUBLICATIONS

Wiesenfeldt ("Selective Arene Hydrogenation for Direct Access to Saturated Carbo- and Heterocycles" Angew. Chem. Int. Ed. 2019, 58, p. 10460-10476) (Year: 2019).*
(Continued)

Primary Examiner — Amy C Bonaparte
(74) Attorney, Agent, or Firm — Marshall, Gerstein & Borun LLP (57) ABSTRACT Process for hydrogenating aromatic compounds over a solid catalyst in the presence of a hydrogen-containing gas comprising a first reactor operated in loop mode, a second reactor operated in straight pass, at least part of the output of the first reactor is supplied to the second reactor, characterized in that the first reactor is configured as a trickle bed reactor and is operated in trickle bed mode and the second reactor is operated such that the catalyst present therein is partially flooded.

14 Claims, 2 Drawing Sheets (51) Int. Cl.
    *B01J 19/32*     (2006.01)
    *C07C 69/78*     (2006.01)
    *C07C 69/82*     (2006.01)
    *C07C 69/74*     (2006.01)
    *C07C 69/753*    (2006.01)
    *C07C 69/75*     (2006.01)

(52) U.S. Cl.
    CPC ............... *B01J 19/32* (2013.01); *C07C 69/78* (2013.01); *C07C 69/82* (2013.01); *B01J 2219/00162* (2013.01); *B01J 2219/185* (2013.01); *C07C 69/74* (2013.01); *C07C 69/75* (2013.01); *C07C 69/753* (2013.01); *C07C 2523/46* (2013.01); *C07C 2601/14* (2017.05)

(56) References Cited

U.S. PATENT DOCUMENTS 7,435,848 B2    10/2008   Grass et al.
8,207,375 B2     6/2012   Grass et al.

FOREIGN PATENT DOCUMENTS

| | | |
|---|---|---|
| DE | 10232868 A1 | 2/2004 |
| EP | 1042273 B1 | 5/2003 |
| EP | 1676828 A2 | 7/2006 |
| WO | WO-2015/082676 A1 | 6/2015 |
| WO | WO-2017/060352 A1 | 4/2017 |
| WO | WO-2019/008561 A1 | 1/2019 |

OTHER PUBLICATIONS

Qi ("Application of supported metallic catalysts in catalytic hydrogenation of arenes" RSC Advances, 2013, 3, p. 14219-14232) (Year: 2013).*

English language translation of DE10036172 (DE '172, published on Mar. 8, 2001, of record in the IDS filed on Dec. 19, 2019) (Year: 2001).*

International Application No. PCT/IB2018/055292, International Search Report, dated Sep. 19, 2018.

* cited by examiner

FIG.1

FIG.2

HYDROGENATION OF AROMATIC COMPOUNDS

CROSS-REFERENCE TO RELATED APPLICATIONS

This application is the U.S. National Stage application of International Patent Application No. PCT/162018/055292, filed Jul. 17, 2018, which claims the benefit of European Patent Application No. 17179827.5, filed Jul. 5, 2017.

The present invention relates to a process for hydrogenating aromatic compounds over a solid catalyst, in particular to a process for preparing alicyclic carboxylic acid esters by hydrogenating the corresponding aromatic carboxylic esters over a solid catalyst.

Processes for hydrogenating aromatic compounds are of central importance in the chemical industry. They serve, for example, the preparation of alicyclic carboxylic acids or alicyclic carboxylic acid esters by hydrogenating aromatic carboxylic acids or aromatic carboxylic acid esters.

Alicyclic carboxylic acid esters, such as the esters of cyclohexane-1,2-dicarboxylic acid, are used as a component of lubricants, adhesives, paints or varnishes, or as auxiliaries in metalworking. Furthermore, they are used as plasticizers for polyolefins or PVC use.

Processes for hydrogenating aromatic carboxylic acid esters to the corresponding alicyclic carboxylic acid esters are known to the person skilled in the art.

For example, DE 102 32 868 A1 or DE 102 25 565 A1 describe the hydrogenation of aromatic polycarboxylic acid esters in two reactors connected in series, the first reactor being operated in loop mode (partial recycling of the reactor output) and the second reactor being operated in straight pass. Hydrogenation is carried out in the liquid/gas mixed phase or the liquid phase.

It is an object of the present invention to provide an improved process for hydrogenating aromatic compounds, in particular aromatic carboxylic acid esters. The improved process should make it possible to make better use of the catalyst. An improved catalyst utilization is evident, for example, in the fact that, at the same hydrogenation temperature, a higher hydrogenation conversion is achieved or, for a certain hydrogenation conversion, a lower hydrogenation temperature is required. The fact that a certain hydrogenation conversion can be achieved at a lower hydrogenation temperature means that the lifetime of the catalyst is, for example, lengthened, due to which longer operating intervals should be possible. A lower hydrogenation temperature should also contribute to less by-product formation. In addition, the process according to the invention is intended to make it possible to better utilize the hydrogen supplied to the hydrogenation process, thus reducing losses of hydrogen unused for hydrogenation.

This object is achieved by a process for hydrogenating aromatic compounds over a solid catalyst in the presence of a hydrogen-containing gas comprising
a first reactor operated in loop mode,
a second reactor operated in straight pass,
wherein at least part of the output of the first reactor is supplied to the second reactor, characterized in that
the first reactor is configured as a trickle bed reactor and is operated in trickle bed mode, and the second reactor is operated such that the catalyst present therein is partially flooded.

In the process according to the invention, hydrogenation of the aromatic compounds is carried out continuously or discontinuously. Preferably, hydrogenation is carried out continuously.

In the process according to the invention, aromatic compounds are hydrogenated to their alicyclic compounds. Aromatic compounds which can be used in the process according to the invention are, for example, phenols, aromatic carboxylic acids or aromatic carboxylic esters. Aromatic carboxylic acids or aromatic carboxylic esters are preferred. Aromatic carboxylic acid esters are particularly preferred.

Aromatic carboxylic acids may have one or more carboxylic acid groups. For example, aromatic carboxylic acids have one, two or three carboxylic acid groups. The carboxylic acid groups are connected via their carbonyl carbon with an aromatic ring. Aromatic carboxylic acids have one or more aromatic rings. For example, in the case of multiple aromatic rings, the aromatic rings may be fused and/or bridged. If the aromatic carboxylic acid has several aromatic rings and several carboxylic acid groups, the carboxylic acid groups may be on one aromatic ring or on different aromatic rings.

Aromatic carboxylic acids having a carboxylic acid group are referred to as aromatic monocarboxylic acids. Aromatic monocarboxylic acids are, for example, benzoic acid or 1-naphthoic acid, with benzoic acid being preferred.

Aromatic carboxylic acids having two carboxylic acid groups are referred to as aromatic dicarboxylic acids. Aromatic dicarboxylic acids are, for example, phthalic acid, isophthalic acid, terephthalic acid, 1,2-naphthalenedicarboxylic acid, 1,3-naphthalenedicarboxylic acid, 1,4-naphthalenedicarboxylic acid, 1,5-naphthalenedicarboxylic acid, 1,7-naphthalenedicarboxylic acid or 1,8-naphthalenedicarboxylic acid, with phthalic acid, isophthalic acid or terephthalic acid being preferred.

Aromatic carboxylic acids having more than two carboxylic acid groups are referred to as aromatic polycarboxylic acids. Aromatic polycarboxylic acids are, for example, hemimellitic acid, trimellitic acid, trimesic acid or benzene-1,2,3,4-tetracarboxylic acid, with trimellitic acid being preferred.

Aromatic carboxylic acid esters are obtained, for example, by esterification of aromatic carboxylic acids with alcohols or by transesterification of aromatic carboxylic acid esters. If an aromatic carboxylic acid has more than one carboxylic acid group, it is generally preferred to esterify each carboxylic acid group as far as possible. The carboxylic acid groups may be independently esterified with the same or with different alcohols. In general, the carboxylic acid groups are preferably esterified with the same alcohol or with a mixture of isomers of an alcohol.

Esterification reactions and transesterification reactions are known to the person skilled in the art (see, for example, WO 2015/082676).

Due to an incomplete esterification, it may be that at least a part of the aromatic carboxylic acid groups is not esterified. Thus, during esterification, mixtures of aromatic carboxylic acid esters with different degrees of esterification may also be formed. Thus during esterification, for example, any mixtures of aromatic monocarboxylic acid esters, aromatic dicarboxylic acid esters and aromatic polycarboxylic acid esters may be formed, depending on the starting compounds.

An alcohol is a single chemical compound or a mixture of isomers. An alcohol may have one or more hydroxy groups. An alcohol having one hydroxy group is called a monool. An alcohol having two hydroxy groups is called a diol. An alcohol having more than two hydroxy groups is called a polyol.

An alcohol preferably has 1 to 18, more preferably 3 to 13, particularly preferably 8 to 13, and most preferably 9 carbon atoms.

An alcohol is, for example, linear or branched. An alcohol is, for example, an alkyl, cycloalkyl or alkoxyalkyl alcohol. Preferably, an alcohol is an alkyl alcohol. More preferably, an alcohol is an alkylmonool.

An alkylmonool with 8 to 13 carbon atoms is, for example, n-octanol, isooctanoyl, 2-ethylhexanol, n-nonanol, 2-propylhexanol, isononanol, n-decanol, isodecanol, 2-propylheptanol, nundecanol, isoundecanol, n-dodecanol, isododecanol, n-tridecanol or iso-tridecanol. Alkyl monools with 9 carbon atoms are preferred. Isononanol is particularly preferred.

Isooctanol, isononanol, isodecanol, isoundecanol, isododecanol or isotridecanol are not single compounds but a mixture of different isomers. The exact composition of such an isomer mixture depends on the preparation conditions and/or the starting compounds used. Depending on the preparation conditions and/or the starting compounds used, compositions of possible isomer mixtures are disclosed by way of example in WO 2015/082676.

The abovementioned alcohols or isomer mixtures can be prepared by methods known to the person skilled in the art (see for example Ullmann's Encyclopedia of Industrial Chemistry, 2013 Wiley-VCH, doi: 10.1002/14356007.a01_279.pub2 or WO 2015/082676).

Aromatic carboxylic esters having an ester group are referred to as aromatic monocarboxylic acid esters. Aromatic monocarboxylic esters are, for example, monomethyl phthalate, monoglycol phthalate, monomethyl terephthalate, monoglycol terephthalate, monomethyl isophthalate or monoglycol isophthalate.

Aromatic monocarboxylic esters are, for example, benzoic acid esters. Benzoic acid may be esterified with monools, diols or polyols. Benzoic acid esters with monools are, for example, isooctyl benzoate, 2-ethylhexyl benzoate, isononyl benzoate, isodecyl benzoate or 2-propyl heptylbenoate. Examples of benzoic acid esters with diols are glycol dibenzoate, diethylene glycol dibenzoate, triethylene glycol dibenzoate or propylene glycol dibenzoate.

Among the aromatic monocarboxylic acid esters, isononylbenzoate, isodecylbenzoate or 2-propylheptylbenzoate are preferred. Isononyl benzoate or isodecyl benzoate are particularly preferred.

Aromatic carboxylic acid esters having two ester groups are referred to as aromatic dicarboxylic acid esters. Aromatic dicarboxylic acid esters are, for example, phthalic diesters, isophthalic diesters, terephthalic diesters, 1,2-naphthalenedicarboxylic acid diesters, 1,3-naphthalenedicarboxylic acid diesters, 1,4-naphthalenedicarboxylic acid diesters, 1,5-naphthalenedicarboxylic acid diesters, 1,7-naphthalenedicarboxylic acid diesters or 1,8-naphthalenedicarboxylic acid diesters, with phthalic diesters or terephthalic diesters being preferred. Phthalic diesters are particularly preferred.

Phthalic acid diesters are, for example, dimethyl phthalate, diethyl phthalate, di-n-propyl phthalate, diisopropyl phthalate, di-n-butyl phthalate, diisobutyl phthalate, di-tert-butyl phthalate, diglycol phthalate, n-octyl phthalate, isooctyl phthalate, di-2-ethylhexyl phthalate, di-n-nonyl phthalate, diisononyl phthalate. Di-n-decyl phthalate, diisodecyl phthalate, di-2-propylheptyl phthalate, di-n-undecyl phthalate, diisoundecyl phthalate, di-n-dodecyl phthalate or diisododecyl phthalate. Diisononyl phthalate, diisodecyl phthalate or di-2-propylheptyl phthalate are preferred. Diisononyl phthalate or di-2-propylheptyl phthalate are further preferred. Diisononyl phthalate is particularly preferred.

Examples of terephthalic diesters are dimethyl terephthalate, diethyl terephthalate, di-n-propyl terephthalate, diisopropyl terephthalate, di-n-butyl terephthalate, diisobutyl terephthalate, di-tert-butyl terephthalate, diglycol terephthalate, n-octyl terephthalate, isooctyl terephthalate, di-2-ethylhexyl terepthalate, di-n-nonyl terephthalate, diisononyl terephthalate, di-n-decyl terephthalate, diisodecyl terephthalate, di-2-propylheptyl terephthalate, din-undecyl terephthalate, diisoundecyl terephthalate, di-n-dodecyl terephthalate or diisododecyl terephthalate. Di-2-ethylhexyl terepthalate is preferred.

Among the aromatic dicarboxylic acid esters, diisononyl phthalate, diisodidecyl phthalate, di-2-propylheptyl phthalate or di-2-ethylhexyl terephthalate are preferred. Diisononyl phthalate or di-2-ethylhexyl terephthalate are further preferred. Diisononyl phthalate is particularly preferred.

Aromatic carboxylic acid esters having more than two ester groups are also referred to as aromatic polycarboxylic acid esters. Aromatic polycarboxylic acid esters are obtained, for example, by esterification of hemimellitic acid, trimellitic acid, trimesic acid or benzene-1,2,3,4-tetracarboxylic acid with an alcohol or a mixture of alcohols.

The main products obtained by the process according to the invention by hydrogenating the aromatic compounds depend, for example, on the hydrogenation conditions, such as temperature and/or pressure and/or the catalyst used. The main products of hydrogenation are also referred to as hydrogenation products in the context of the present invention.

In the present invention, alicyclic compounds are obtained as hydrogenation products in the hydrogenation of aromatic compounds. When the aromatic compounds are aromatic carboxylic acids, the alicyclic carboxylic acids are obtained as hydrogenation products. When the aromatic compounds are aromatic carboxylic acid esters, the alicyclic carboxylic esters are obtained as hydrogenation products.

Thus, for example, by the process according to the invention, di(isononyl)-1,2-cyclohexanedicarboxylate can be obtained as the hydrogenation product from diisononyl phthalate, di-(2-propylheptyl)-1,2-cyclohexanedicarboxylate can be obtained from di-2-propylheptyl phthalate, di-2 (isodecyl)-1,2 cyclohexanedicarboxylate can be obtained from diisodecyl phthalate or di-(2-ethylhexyl)-1,4 cyclohexanedicarboxylate can be obtained from di-2-ethyl hexyl terepthalate.

In the process according to the invention, the aromatic compounds are hydrogenated over a solid catalyst in the presence of a hydrogen-containing gas. Preferably, the aromatic compounds are continuously hydrogenated over a solid catalyst in the presence of a hydrogen-containing gas.

Preferably, the catalyst is arranged in the fixed bed as a random bed or as a packing in the first and second reactors. More preferably, the catalyst in the fixed bed is arranged as a random bed in the first and second reactors. A reactor may contain one or more catalyst beds connected in series. For multiple series catalyst beds, the length of the catalyst beds may vary.

Preferably, the catalyst volume is distributed according to a ratio of 85:15 to 60:40 between the first and second reactor.

For the hydrogenation of aromatic compounds, preferably for the hydrogenation of aromatic carboxylic acids or aromatic carboxylic acid esters to the corresponding alicyclic carboxylic acids or alicyclic carboxylic acid esters, the catalyst preferably contains metals and/or metal oxides from subgroups VI to VIII of the Periodic Table of the Elements, in particular platinum, rhodium, palladium, cobalt, nickel and/or ruthenium as the catalytically active component, with ruthenium being particularly preferred. Such a catalyst may also contain metals and/or metal oxides from subgroups V or IX of the Periodic Table of the Elements, in particular rhenium and/or copper. The metals and/or metal oxides may be deposited on a carrier material. If the metals and/or metal oxides are deposited on a carrier material, a carrier material having an average pore diameter in the range of 2 to 50 nm is generally used in the preparation of such a catalyst (the determination of the average pore diameter is carried out by Hg porosimetry, in particular according to DIN 66133). The carrier material may contain activated carbon, silicon carbide, alumina, silica, aluminosilicate, titania, zirconia, magnesia, zinc oxide or a mixture of two or more of said components. The carrier material may also contain alkali metals, alkali metal oxides, alkaline earth metals, alkaline earth metal oxides and/or sulfur. Catalysts which are preferred for hydrogenating aromatic compounds, in particular aromatic carboxylic acids or aromatic carboxylic acid esters, are described, for example, in EP-B1 104227361, DE-A 10232868, DE-A 10225565 or EP-A2 1676828. A preferred catalyst has, for example, an Ru content of 0.45 to 0.55 percent by weight based on the weight of the carrier material, a specific surface area of 220 to 290 $m^2/g$ (BET, ISO 9277) and a pore volume of 0.48 to 0.62 mL/g (Hg porosimetry, DIN 66133), the carrier material comprising alumina. Another preferred catalyst has, for example, an Ru content of 0.3 to 0.45 percent by weight based on the weight of the carrier material, a specific surface area of 310 to 360 $m^2/g$ (BET, ISO 9277) and a pore volume of 0.7 to 0.9 mL/g (Hg porosimetry, DIN 66133), the carrier material comprising silicon oxide.

A hydrogen-containing gas is any hydrogen-containing gas mixture that does not contain harmful amounts of catalyst poisons such as carbon monoxide and/or sulfur compounds. A hydrogen-containing gas may contain an inert medium. An inert medium does not react with the educts, products and the catalyst under the reaction conditions. An inert medium may be nitrogen, methane, helium, argon, or a mixture of these. Preferably, hydrogen that is as pure as possible is used as the hydrogen-containing gas. Hydrogen that is as pure as possible has a purity of at least 90 percent, preferably at least 95 percent and more preferably at least 98 percent. The use of hydrogen that is as pure as possible has the advantage that the accumulation of the inert medium in the reaction space is reduced. An accumulation of the inert medium in the reaction space would lead to a reduction of the hydrogen partial pressure, which would have a negative effect on the space-time yield of the hydrogenation reaction.

According to the process of the invention, aromatic compounds, preferably aromatic carboxylic esters, may be continuously hydrogenated over a solid catalyst and in the presence of a hydrogen-containing gas having a hydrogen content of at least 95 percent and preferably at least 98 percent.

The amount of hydrogen used in the process according to the invention is at least equal to the stoichiometric amount required to hydrogenate the aromatic compounds. However, an excess of up to 30 percent above the stoichiometrically required amount is preferably used for hydrogenation. More preferably, an excess of up to 20 percent and particularly preferably an excess of up to 10 percent above the stoichiometrically required amount is used.

The process according to the invention for hydrogenating aromatic compounds comprises a first reactor operated in loop mode and a second reactor operated in straight pass. The second reactor is connected to the first reactor such that at least part of the output of the first reactor is supplied to the second reactor. Preferably, the first and second reactors are tubular reactors, in particular vertical tubular reactors. Preferably, the first and the second reactors have no heating or cooling devices.

Instead of the first reactor, which is operated in loop mode, it is also possible to use a plurality of reactors operated in loop mode and connected in series or in parallel. Instead of the second reactor, which is operated in straight pass, it is also possible to use a plurality of reactors operated in straight pass and connected in series or in parallel. However, preferably only one loop mode reactor and one straight pass reactor are used.

Each of the reactors may contain one or more catalyst beds with the catalyst beds connected in series. The catalyst beds may vary in length.

The first loop mode reactor is configured as a trickle bed reactor and is operated in trickle bed mode. Although not preferred, it is generally possible to operate the first reactor as a loop reactor in liquid phase mode.

Circulating current and fresh feed are supplied as a feed to the first reactor. For this purpose, for example, the circulating current can be mixed with the fresh feed and the mixture supplied to the first reactor. The circulating current and fresh feed may also be supplied separately to the first reactor. The fresh feed contains aromatic compounds which are to be hydrogenated in the context of the process according to the invention. Preferably, the liquid loading of the catalyst with fresh feed is 50 to 1000 $kg_{fresh\ feed}/(hour*m^3_{total\ catalyst\ volume})$. The total catalyst volume is the catalyst volume distributed over the reactors used. More preferably, the liquid loading of the catalyst with fresh feed is 100 to 500 $kg_{fresh\ feed}/(hour*m^3_{total\ catalyst\ volume})$.

The feed preferably has a temperature of 70 to 150° C. and more preferably a temperature of 80 to 120° C. when it is supplied to the first reactor. For example, the feed has a temperature of 85, 90, 95, 100, 105, 110 or 115° C. If the circulating current and the fresh feed are supplied to the first reactor separately, they preferably have a temperature of from 70 to 150° C. and more preferably a temperature of from 80 to 120° C., independently of one another. Thus, for example, the circulating current and the fresh feed may, independently of one another, have a temperature of 85, 90, 95, 100, 105, 110 or 115° C.

The output from the first reactor is separated into a circulating current and a hydrogenation current. The circulating current is returned to the first reactor; the hydrogenation current is supplied to the second reactor for further hydrogenation. The separation of the output from the first reactor into a circulating current and a hydrogenation current can be carried out by current separation methods known to the person skilled in the art, for example by means of a pump device with overflow, or a current divider. Preferably, the circulating current is cooled before being returned to the first reactor. The output is taken from the lower part of the reactor, for example at the bottom.

Preferably, the circulation ratio between the circulating current and the hydrogenation current is 1:1 to 20:1. More preferably, the circulation ratio is 2:1 to 15:1. Particularly preferably, the circulation ratio is 4:1 to 10:1. For example, the circulation ratio is 5:1, 6:1, 7:1, 8:1 or 9:1.

In the output from the first reactor, the hydrogenation conversion of the aromatic compounds is preferably 80 to 98 percent based on the total hydrogenation conversion in the first and second reactors, more preferably 85 to 95 percent.

If, for example, aromatic carboxylic acids or aromatic carboxylic acid esters are used as aromatic compounds, the hydrogenation conversion is preferably 80 to 98 percent, based on the total hydrogenation conversion in the first and second reactors and more preferably 85 to 95 percent. For example, the hydrogenation conversion in the first reactor is 86, 88, 90, 92 or 94 percent.

Since the output from the first reactor usually has a higher temperature than the fresh feed when it is supplied to the first reactor, the output from the first reactor may be cooled before it is separated into a circulating current and a hydrogenation current. The circulating current may also be cooled after separation of the output from the first reactor. The cooling of the output and/or the circulating current can take place in one or more heat exchangers. It may be advantageous to heat-couple the cooling of the output and/or the circulating current with the heating of the fresh feed.

Preferably, the circulation ratio between the circulating current and the fresh feed is 1:1 to 20:1 in the first reactor. More preferably, the circulation ratio is 2:1 to 15:1. Particularly preferably, the circulation ratio is 4:1 to 10:1. For example, the circulation ratio may be 5:1, 6:1, 7:1, 8:1 or 9:1.

The circulating current and fresh feed are supplied to the first reactor in such a way that a distribution of the liquids that is as uniform as possible across the reactor cross-section is ensured. This has the advantage of a catalyst utilization that is as uniform as possible. The circulating current and fresh feed can be supplied via one or more feeders distributed over the reactor cross-section. The feeders are located in the upper part of the reactor, above the catalyst. Furthermore, one or more distribution devices, such as distributor plates, may be arranged in the reactor above the catalyst and below the feeders.

The liquid loading of the catalyst (superficial velocity) in the first reactor is preferably 30 to 180 m/h, more preferably 50 to 150 m/h and particularly preferably 60 to 120 m/h. For example, the superficial velocity in the first reactor is 70, 80, 85, 90, 95, 100, 105, 110 or 115 m/h. A sufficiently high liquid loading ensures complete wetting of the entire catalyst bed. This avoids liquid strands forming and a part of the catalyst remaining unused. Incidentally, the higher the liquid loading, the more intensive the exchange of substances becomes. As a result, the space-time yield can be positively influenced, for example.

The hydrogenation of aromatic compounds may be carried out in the absence or in the presence of an inert solvent. Suitable inert solvents are all liquids which, under the reaction conditions, do not react with the educts, products and the catalyst, which form homogeneous solutions with the educts and products and can easily be separated from the products. The inert solvent may also be a mixture of different liquids. An inert solvent may be, for example, the hydrogenation product of the particular hydrogenation process, an isomer mixture of long-chain hydrocarbons, or an isomer mixture of alcohols having 9 to 13 carbon atoms.

The use of an inert solvent has the advantage, for example, that the temperature development of the hydrogenation can be better controlled.

If the hydrogenation of aromatic compounds is carried out in the presence of an inert solvent, the inert solvent may be supplied to the first reactor with the circulating current and/or the fresh feed. The inert solvent may be mixed with the circulating current and/or the fresh feed before the resulting mixture is supplied to the first reactor.

If the first reactor has a plurality of catalyst beds connected in series, the inert solvent may also be supplied to the first reactor between the catalyst beds. This is possible regardless of whether the inert solvent is supplied to the first reactor with the circulating current and/or the fresh feed. If the inert solvent is supplied to the first reactor between the catalyst beds, it can be mixed with hydrogen-containing gas.

The hydrogen-containing gas is supplied to the first reactor. The hydrogen-containing gas is supplied to the first reactor separately or mixed with the circulating current and/or fresh feed. Preferably, the hydrogen-containing gas is supplied to the first reactor separately from the circulating current and/or fresh feed. If the hydrogen-containing gas is supplied separately to the first reactor, this may take place via one or more feeders distributed over the reactor cross-section. The hydrogen-containing gas is supplied to the first reactor in cocurrent or countercurrent. Preferably, the hydrogen-containing gas is supplied to the first reactor in cocurrent. If the hydrogen-containing gas is supplied to the first reactor in cocurrent, one or more feeders for the hydrogen-containing gas are generally in the upper part of the reactor, above the catalyst.

If the first reactor has a plurality of catalyst beds connected in series, part of the hydrogen-containing gas can also be supplied to the first reactor between the catalyst beds. This can have the advantage that the heat development of the hydrogenation reaction can be better controlled. For this purpose, the hydrogen-containing gas can be supplied to the first reactor directly or mixed with an inert solvent.

The hydrogenation of the aromatic compounds in the first reactor may be carried out adiabatically, polytropically or practically isothermally, that is with a temperature increase of typically less than 10 to 15° C.

In general, hydrogenating aromatic compounds in the first reactor largely adiabatically is preferred. The hydrogenation of aromatic compounds is carried out so that the output at the outlet of the first reactor preferably has a temperature of 90 to 180° C. or less. More preferably, the output at the outlet of the first reactor has a temperature of 90 to 160° C. or less.

The temperature of the output at the outlet of the first reactor depends, for example, on the temperature of the fresh feed, the temperature of the circulating current supplied to the first reactor, the hydrogenation conversion in the first reactor, the ratio of fresh feed to circulating current and/or the ratio of hydrogenation current to circulating current.

For hydrogenation of aromatic compounds, the pressure in the first reactor is preferably 50 to 500 bar, more preferably 100 to 400 bar and particularly preferably 200 to 280 bar. For example, the pressure in the first reactor may be 210, 220, 230, 240, 250, 260 or 270 bar.

If aromatic carboxylic acids or aromatic carboxylic esters are used as aromatic compounds, the pressure in the first reactor is preferably 50 to 500 bar, more preferably 100 to 400 bar, particularly preferably 150 to 300 bar, and particularly preferably 200 to 280 bar. For example, the pressure in the first reactor may be 210, 220, 230, 240, 250, 260 or 270 bar.

The second reactor is operated in straight pass. The catalyst in the second reactor is partially flooded. Preferably, the non-flooded part of the catalyst in the second reactor is operated in trickle mode. A flooding of the catalyst can be generated by accumulating the feed of the second reactor and maintaining its level. Methods for the accumulation and maintenance of liquids in reactors or in containers are known to the person skilled in the art. The degree of flooding of the catalyst can be controlled, for example, by a differential pressure measurement in combination with a control of the output volume current from the second reactor.

In a partial flooding of the catalyst, part of the catalyst volume is surrounded by a continuous liquid phase. Preferably, the catalyst in the second reactor is flooded such that 10 to 98 percent of the catalyst volume is surrounded by a continuous liquid phase. More preferably, 15 to 95 percent of the catalyst volume is surrounded by a continuous liquid phase. Particularly preferably, 50 to 95 percent of the catalyst volume is surrounded by a continuous liquid phase. Thus, for at least partial flooding of the catalyst, 55, 60, 65, 70, 75, 80, 85 or 90 percent of the catalyst volume may, for example, be surrounded by a continuous liquid phase.

The hydrogenation current forms the feed for the second reactor. The hydrogenation current is supplied to the upper part of the second reactor, above the catalyst. Preferably, the hydrogenation current is supplied to the second reactor in such a way that the most uniform possible distribution of the hydrogenation current over the reactor cross-section is ensured. This has the advantage of a catalyst utilization that is as uniform as possible. The hydrogenation current may be supplied via one or more feeders distributed over the reactor cross-section. The feeders are located in the upper part of the reactor, above the catalyst. Furthermore, one or more distribution devices, such as distributor plates, may be arranged in the reactor above the catalyst and below the feeders. As a rule, no fresh hydrogen-containing gas is supplied to the second reactor, although this is generally possible.

The hydrogenation current preferably has a temperature of 80 to 180° C. and more preferably a temperature of 90 to 160° C. when it is supplied to the second reactor. For example, the hydrogenation current may have a temperature of 95, 105, 110, 115, 120, 125, 130, 135, 140, 145, 150 or 155° C. when it is supplied to the second reactor. In order to set a corresponding temperature of the hydrogenation current, it can be heated or cooled by means of a heat exchanger, for example.

In a preferred embodiment, the second reactor in the form of a vertical tubular reactor comprises a free space in the upper part and a first and a second compartment in the lower part. The first compartment is configured as an upwardly open cylinder and forms an annulus. The second compartment forms an annular gap space surrounding the annulus. The first compartment is essentially arranged concentrically in the second reactor. The outer wall of the first compartment and the inner wall of the second reactor form the annular gap space. The annulus and the annular gap space surrounding the annulus are open toward the top of the reactor. The annulus and the annular gap space surrounding the annulus are not fluidly connected to each other in the plane of their cross-sections. The lower part of the second reactor preferably extends over the bottom 30 to 80 percent of the internal volume of the reactor. The upper part of the second reactor preferably extends over the upper 70 to 20 percent of the internal volume of the reactor.

The output of the first reactor is supplied to the second reactor in the upper part of the second reactor in the area of the free space. The output of the first reactor is preferably supplied to the second reactor in such a way that a distribution of the output from the first reactor that is as uniform as possible over the reactor cross-section of the second reactor is ensured. For this purpose, the output from the first reactor may be supplied via one or more feeders distributed over the reactor cross-section. The feeders are located in the upper part of the reactor in the area of the free space. One or more distribution devices, such as distribution plates, may also be arranged in the upper part and below the feeders.

The catalyst is arranged either in the annulus or in the annular gap space. Preferably, the catalyst is arranged in the annulus. The annulus or annular gap space may contain one or more catalyst beds. If the annulus or annular gap space contains a plurality of catalyst beds, these are usually connected in series. The length of the individual catalyst beds may vary.

The compartment containing the catalyst is operated in straight pass with the catalyst partially flooded. The part of the catalyst which is not flooded is preferably operated in trickle mode.

The compartment which does not contain the catalyst is connected to the first reactor in a liquid-conductive manner. The part of the feed of the second reactor which is supplied to this compartment is at least partially recycled to the first reactor and thus represents the circulating current. This has the advantage, for example, that the output from the first reactor can be supplied to the second reactor without prior separation into a hydrogenation current and a circulating current.

Thus, it may be preferred that the second reactor in the form of a vertical tubular reactor comprises a first compartment configured as an upwardly open cylinder that is essentially arranged concentrically for receiving the catalyst and a second compartment configured as an annulus between the outer wall of the first compartment and the inner wall of the reactor for receiving a liquid phase volume. More preferably, the second compartment is connected to the first reactor in a liquid-conductive manner.

If the catalyst is arranged in the first compartment, it is particularly preferred for the second compartment to be connected to the first compartment in a fluid-continuous manner via an overflow. The outflow from the first reactor is supplied to the second reactor so that the entire feed of the second reactor is first supplied to the second compartment. This can be achieved, for example, by a suitable arrangement of the feeders and/or distribution devices. Such an arrangement has the advantage that a volume of liquid is always kept in the second compartment. Only when a certain liquid level is reached does the liquid phase pass from the second compartment into the first compartment and pass through the catalyst arranged therein. Preferably, the overflow is designed in such a way that a distribution of the liquid passing over the catalyst that is as uniform as possible is allowed. This is possible, for example, by distribution devices arranged in the first compartment. Such an embodiment of the second reactor is described, for example, in DE 100 36 172 A1, the contents of which, with regard to the second hydrogenation reactor described therein, are referred to in their entirety. In this case, the second compartment is connected in a liquid-conductive manner to the first reactor, with which at least part of the feed into the second compartment is recycled as a circulating current into the first reactor.

As a result of the described configuration of the second reactor, the output from the first reactor, which is supplied to the second reactor, is separated within the second reactor into a circulating current and a hydrogenation current. The part of the output of the first reactor which is supplied to the compartment containing the catalyst within the second reactor represents the hydrogenation current. The part of the output of the first reactor which is taken from the compartment within the second reactor which contains no catalyst and is recycled to the first reactor represents the circulating current.

The liquid loading of the catalyst (superficial velocity) in the second reactor is preferably 5 to 100 m/h, more preferably 10 to 80 m/h, and particularly preferably 15 to 70 m/h.

The liquid loading of the catalyst in the second reactor is, for example, 20, 25, 30, 35, 40, 45, 50, 55, 60 or 65 m/h.

The hydrogenation of the aromatic compounds in the second reactor may be carried out adiabatically, polytropically or practically isothermally, that is with a temperature increase of typically less than 10 to 15° C.

In general, hydrogenating aromatic compounds in the first reactor adiabatically is preferred. The hydrogenation of aromatic compounds is carried out so that the output at the outlet of the second reactor has a temperature of 220° C. or less. Preferably, the output at the outlet of the second reactor has a temperature of 180° C. or less. Thus, the output at the outlet of the second reactor has a temperature of 100 to 220° C., for example. Preferably, the output at the outlet of the second reactor may have a temperature of 100 to 180° C. The output is taken from the lower part of the second reactor, for example at the bottom. If the second reactor has a first and a second compartment, the output is taken from the compartment containing the catalyst. The output is preferably taken from the lower part of the corresponding compartment, for example at the bottom.

For hydrogenating aromatic compounds, the pressure in the second reactor is preferably 50 to 500 bar. More preferably, the pressure in the second reactor is 100 to 400 bar, particularly preferably 200 to 280 bar.

If aromatic carboxylic acids or aromatic carboxylic esters are used as aromatic compounds, the pressure in the second reactor is preferably 50 to 500 bar, more preferably 100 to 400 bar, and particularly preferably 210 to 280 bar. For example, the pressure in the second reactor may be 220, 230, 240, 250, 260 or 270 bar.

In general, the first and second reactors preferably have a common pressure maintenance and therefore present comparable pressures in both reactors. At comparable pressures, the pressures in the first and second reactors differ by a maximum of 10 bar, preferably by a maximum of 2 bar.

The hydrogenation conversion in the second reactor is preferably 2 to 20 percent, based on the total hydrogenation conversion in the first and second reactors, more preferably 5 to 15 percent. If, for example, aromatic carboxylic acids or aromatic carboxylic esters are used as aromatic compounds, the hydrogenation conversion in the second reactor is preferably 2 to 20 percent, based on the total hydrogenation conversion in the first and second reactors, more preferably 5 to 15 percent.

In the output from the second reactor, the hydrogenation conversion of the aromatic compounds is preferably at least 95 percent, more preferably at least 98 percent and most preferably at least 99.9 percent, based on the total hydrogenation in the first and second reactors. Thus, the hydrogenation conversion is preferably 95 to 100 percent, more preferably 98 to 100 percent, and particularly preferably 99.9 to 100 percent. The hydrogenation conversion of the aromatic compounds in the output from the second reactor is, for example, 99.99 percent or more.

If in the process according to the invention aromatic carboxylic acids or aromatic carboxylic acid esters, such as diisononyl phthalate or di-2-ethylhexyl terephthalate, are used as aromatic compounds, the residual aromatic content, based on the hydrogenation products in the output from the second reactor, is preferably not more than 100 ppm, more preferably not more than 50 ppm.

The output from the second reactor can be worked up by methods known to the person skilled in the art in order to isolate the hydrogenation products. For example, the output from the second reactor may be subjected to distillation and/or stripping to isolate the hydrogenation products.

Distillation may be carried out as simple distillation or rectification. Distillation may be carried out in one or more columns connected in series or in parallel. Suitable columns for distillation are tray columns, for example, such as valve tray columns. Columns with packing are preferred. For example, packing is random packing or ordered packing. Ordered packing is preferred. The number of separation stages can be adjusted by the person skilled in the art thanks to their expertise and by a few routine experiments on the desired separation effect.

In stripping, the output is contacted in cocurrent or countercurrent with a stripping medium. A stripping medium is, for example, gases such as water vapor, nitrogen and/or hydrogen.

Stripping may be carried out in one or more columns connected in series or in parallel. Suitable columns for stripping are tray columns, for example, such as valve tray columns. Columns with packing are preferred. For example, packing is random packing or ordered packing. Ordered packing is preferred.

When the hydrogenation products are alicyclic carboxylic acid esters, such as di-(isononyl)-1,2-cyclohexanedicarboxylate, di-(2-propylheptyl)-1,2-cyclohexanedicarboxylate, di-2(isodecyl)-1,2-cyclohexanedicarboxylate or di-(2-ethylhexyl)-1,4-cyclohexanedicarboxylate, they may, for example, be used as plasticizers or as part of plasticizer compositions for plastics such as PVC. Another use of these compounds is, for example, the production of plastisols, in particular PVC plastisols.

When used as plasticizers or in the production of plastisols, it may be advantageous that the compounds mentioned are used together with other plasticizers, advantageously plasticizers which lower the gelling temperature.

Advantages of the Process According to the Invention

One advantage of the process according to the invention is, for example, improved catalyst utilization. Improved catalyst utilization is evident, for example, in the fact that a higher hydrogenation conversion is achieved at the same hydrogenation temperature, or a lower hydrogenation temperature is required for a given hydrogenation conversion. For example, a lower hydrogenation temperature has the advantage of reduced by-product formation. Additionally, a lower hydrogenation temperature generally results in a longer catalyst life, allowing for longer operating intervals.

EXAMPLE

The examples are merely illustrative of the invention and are not intended to be limiting.

Figure 1:
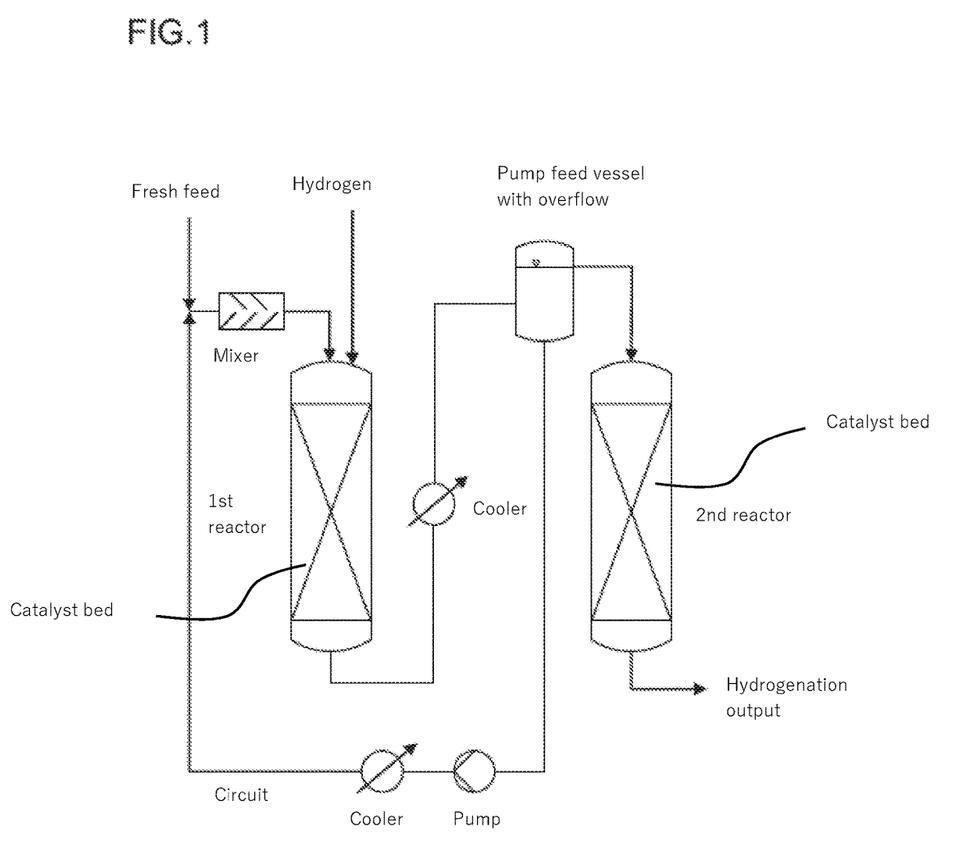
Figure 2:
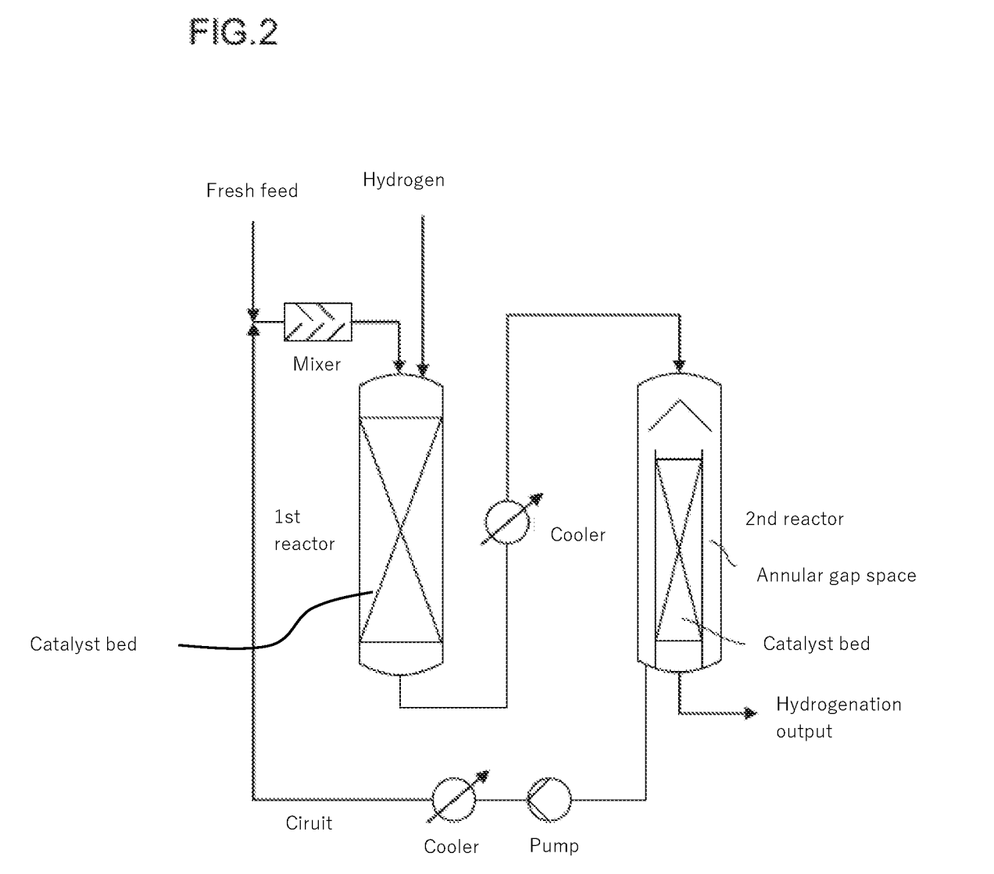

In an industrial hydrogenation plant according to FIG. 1 or FIG. 2, diisononyl phthalate was hydrogenated to di-(isononyl)-1,2-cyclohexanedicarboxylate. Hydrogenation took place in two reactors connected in series. The catalyst was arranged in a fixed bed in both reactors. 72% of the total catalyst volume was in the first reactor; 28% of the total catalyst volume was in the second reactor. The catalyst used had a ruthenium content of 0.5 percent by weight based on the total weight of the carrier material, a specific surface area of 220 to 290 m$^2$/g (BET, ISO9277) and a pore volume of 0.48 to 0.62 mL/g (Hg porosimetry, DIN 66133), the carrier material comprising alumina. The first reactor was operated in loop mode; the second reactor was operated in straight pass.

The hydrogen pressure was 215 bar in both reactors. The hydrogenation plant was operated with a diisononyl phthalate fresh feed of 292 kg/(hour*m³ total catalyst volume). The circulation ratio in the first reactor between the circulating current and the fresh feed was 12:1. Hydrogenation was operated such that, in the output from the second reactor, the residual aromatic content based on di-(isononyl)-1,2-cyclohexanedicarboxylate was less than 100 ppm.

Modes of Operation in Comparison:

The first and the second reactors were operated in trickle bed mode. The following feed temperatures were set:
First reactor: 97° C.
Second reactor: 109° C.

The hydrogen losses during this operation were 3 kg/t di-(isononyl)-1,2-cyclohexanedicarboxylate.

Modes of Operation According to the Invention:

The first reactor was operated in trickle bed mode. In the second reactor, the catalyst was 70% flooded. The following feed temperatures were set:
First reactor: 92° C.
Second reactor: 98° C.

The hydrogen losses during this operation were 0.5 kg/t di-(isononyl)-1,2-cyclohexanedicarboxylate.

Comparison of the Modes of Operation:

Operating points are compared with the same load. By flooding the catalyst in the second reactor, the following advantages were achieved:
Reduction of hydrogen losses
Lowering of the feed temperature of the first reactor by 5° C.
Lowering of the feed temperature of the second reactor by 11° C.

A lower feed temperature increases the remaining service life of the catalyst.

The invention claimed is:

1. Process for hydrogenating an aromatic compound over a solid catalyst in the presence of a hydrogen-containing gas comprising
   supplying a fresh feed comprising the aromatic compound in a liquid form or in a solution in an inert solvent forming a continuous liquid phase and the hydrogen containing gas to a first reactor operated in loop mode,
   taking an output of the first reactor from the lower part of the first reactor,
   separating the output into a circulating current and a hydrogenation current,
   returning the circulating current to the first reactor,
   supplying the hydrogenation current to a second reactor operated in straight pass,
   wherein at least part of the output of the first reactor is supplied to the second reactor, and
   taking an output from the lower part of the second reactor comprising a product,
   wherein
   the catalyst is arranged in a fixed bed as a random bed or as a packing in the first and second reactors and the catalyst contains metals and/or metal oxides from subgroups VI to VIII of the Periodic Table of the Elements,
   the first reactor is configured as a trickle bed reactor and is operated in trickle bed mode,
   and the second reactor is operated such that the catalyst present therein is partially flooded.

2. The process according to claim 1, wherein a non-flooded part of the catalyst in the second reactor is operated in trickle bed mode.

3. The process according to claim 1, wherein a circulation ratio in the first reactor between the circulating current and the fresh feed is 1:1 to 20:1 (by mass).

4. The process according to claim 1, wherein a pressure in the first and second reactors is 50 to 500 bar.

5. The process according to claim 1, wherein a feed temperature for the first reactor is from 70 to 150° C. and a feed temperature for the second reactor is from 80 to 180° C.

6. The process according to claim 1, wherein 10 to 98 percent of a catalyst volume in the second reactor is surrounded by a continuous liquid phase.

7. The process according to claim 1, wherein the aromatic compound is an aromatic carboxylic acid ester and hydrogenated to the corresponding alicyclic carboxylic acid ester.

8. The process according to claim 7, wherein mono-, di- or polycarboxylic acid esters are used as the aromatic carboxylic acid ester.

9. The process according to claim 1, wherein the aromatic compound is diisononyl phthalate or di-2-ethylhexyl terepthalate.

10. The process according to claim 1, wherein the aromatic compound is isononyl benzoate or decyl benzoate.

11. The process according to claim 1, wherein the hydrogenation in the second reactor is 2 to 20 percent based on a total hydrogenation in the first and second reactors.

12. The process according to claim 7, wherein the catalyst comprises a metal of the eighth subgroup of the Periodic Table of the Elements.

13. The process according to claim 12, wherein the catalyst contains ruthenium.

14. The process according to claim 1, wherein the second reactor is a vertical tubular reactor and comprises a first compartment configured as an upwardly open cylinder that is essentially arranged concentrically in the second reactor comprising the catalyst and a second compartment configured as an annulus between the outer wall of the first compartment and the inner wall of the reactor comprising a liquid phase volume.

* * * * *